(12) United States Patent
Spencer et al.

(10) Patent No.: US 7,854,959 B2
(45) Date of Patent: Dec. 21, 2010

(54) CONTROLLED SURFACE CHEMICAL GRADIENTS

(75) Inventors: Nicholas D. Spencer, Zollikon (CH); Sara Maria Morgenthaler, Zurich (CH); Seunghwan Lee, Zurich (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 933 days.

(21) Appl. No.: 10/814,995

(22) Filed: Mar. 31, 2004

(65) Prior Publication Data

US 2004/0224303 A1 Nov. 11, 2004

Related U.S. Application Data

(60) Provisional application No. 60/459,823, filed on Mar. 31, 2003.

(51) Int. Cl.
*G01N 1/31* (2006.01)
(52) U.S. Cl. .................. 427/2.13; 427/466; 427/485; 435/286.2; 435/286.4; 435/286.5; 436/518
(58) Field of Classification Search ................. None
See application file for complete search history.

(56) References Cited

U.S. PATENT DOCUMENTS

| 4,968,535 | A |   | 11/1990 | Terai et al. |   |
|---|---|---|---|---|---|
| 5,656,034 | A | * | 8/1997 | Kochersperger et al. | 604/155 |
| 6,242,264 | B1 | * | 6/2001 | Natan et al. | 436/171 |
| 6,766,817 | B2 |   | 7/2004 | Da Silva |   |
| 6,770,323 | B2 | * | 8/2004 | Genzer et al. | 427/248.1 |
| 2002/0113095 | A1 | * | 8/2002 | Jeon et al. | 222/424.5 |
| 2002/0194930 | A1 | * | 12/2002 | Crosby et al. | 73/827 |

FOREIGN PATENT DOCUMENTS

JP 10-005673 1/1998

OTHER PUBLICATIONS

Bain, et al., "Formation of two-component surfaces by the spontaneous assembly of monolayers on gold from solutions containing mixtures of organic thiols" *J. Am. Chem. Soc.*, 110, 6560-6561 (1988).
Bain, et al., "Formation of monolayer films by the spontaneous assembly of organic thiols from solution onto gold" *J. Am. Chem. Soc.*, 111, 321-335 (1989).

(Continued)

*Primary Examiner*—N Yang
(74) *Attorney, Agent, or Firm*—Pabst Patent Group LLP

(57) ABSTRACT

A simple and reproducible preparative method for the fabrication of surface-chemical gradients is described herein. Surface-chemical gradient films are prepared by using a liquid front in relative motion to the substrate (e.g. immersion by a linear-motion drive or the use of a spreading droplet) to gradually expose substrate samples to very dilute solutions of adsorbates. As demonstrated by XPS, the self-assembled monolayer gradients produced in this way display a high packing density. This method can be used in the preparation of other gradients of various chemical or biochemical functionalities in one or two dimensions. Such gradients can be used in a wide variety of applications in such diverse areas as cell motility studies, nanotribology research, and high-throughput screening.

18 Claims, 3 Drawing Sheets

OTHER PUBLICATIONS

Dertinger, et al., "Generation of gradients having complex shapes using microfluidic networks" *Anal.Chem.*, 73, 1240-1246 (2001).

Fuierer, et al., "Patterning mesoscale gradient structures with self-assembled monolayers and scanning tunneling microscopy based replacement lithography" *Adv.Mater.*, 14, 154-157 (2002).

Herbert, et al., "Micropatterning gradients and controlling surface densities of photoactivatable biomolecules on self-assembled monolayers of oligo(ethylene glycol) alkanethiolates" *Chem. Biol.*, 4, 731-737 (1997).

Jeon, et al., "Generation of solution and surface gradients using microfluidic systems" *Langmuir*, 16, 8311-8316 (2000).

Laibinis, et al., "Attenuation of photoelectrons in monolayers of n-alkanethiols adsorbed on copper, silver, and gold" *J. Phys. Chem.*, 95, 7017-7021 (1991).

Liedberg, et al., "Molecular gradients of ω-substituted alkanethiols on gold: preparation and characterization" *Langmuir* 11, 3821-3827 (1995).

Liedberg, et al., "Molecular gradients of ω-substituted alkanethiols on gold studied by x-ray photoelectron spectrocopy" *Langmuir*, 13, 5329-5334 (1997).

Ruardy, et al., "Preparation and characterization of chemical gradient surfaces and their application for the study of cellular interaction phenomena" *Surf. Sci. Rep.*, 29, 3-30 (1997).

Sehayek, et al., "Preparation of graded materials by laterally controlled template synthesis" *J. Am. Chem. Soc.*, 125, 4718-4719 (2003).

Terrill, et al., "Dynamic monolayer gradients: active spatiotemporal control of alkinethiol coatings on thin gold films" *J. Am Chem. Soc.*, 122, 988-989 (2000).

Wu, et al., "Formation and properties of anchored polymers with a gradual variation of grafting densities on flat substrates" *Macromolecules*, 36, 2448-2453 (2003).

*Hawley's Condensed Chemical Dictionary* (Lewis, R. J., ed.), pp. 837, J. Wiley & Sons, Inc.: New York, 1997.

Morgenthaler, et al., "Surfaces with a hydrophobicity gradient: Possible applications in biological testing" *European Cells and Materials* 6: 69 (2003).

Morgenthaler, et al., "A simple, reproducible approach to the preparation of surface-chemical gradients" *Langmuir* 19(25): 10459-10462 (2003).

* cited by examiner

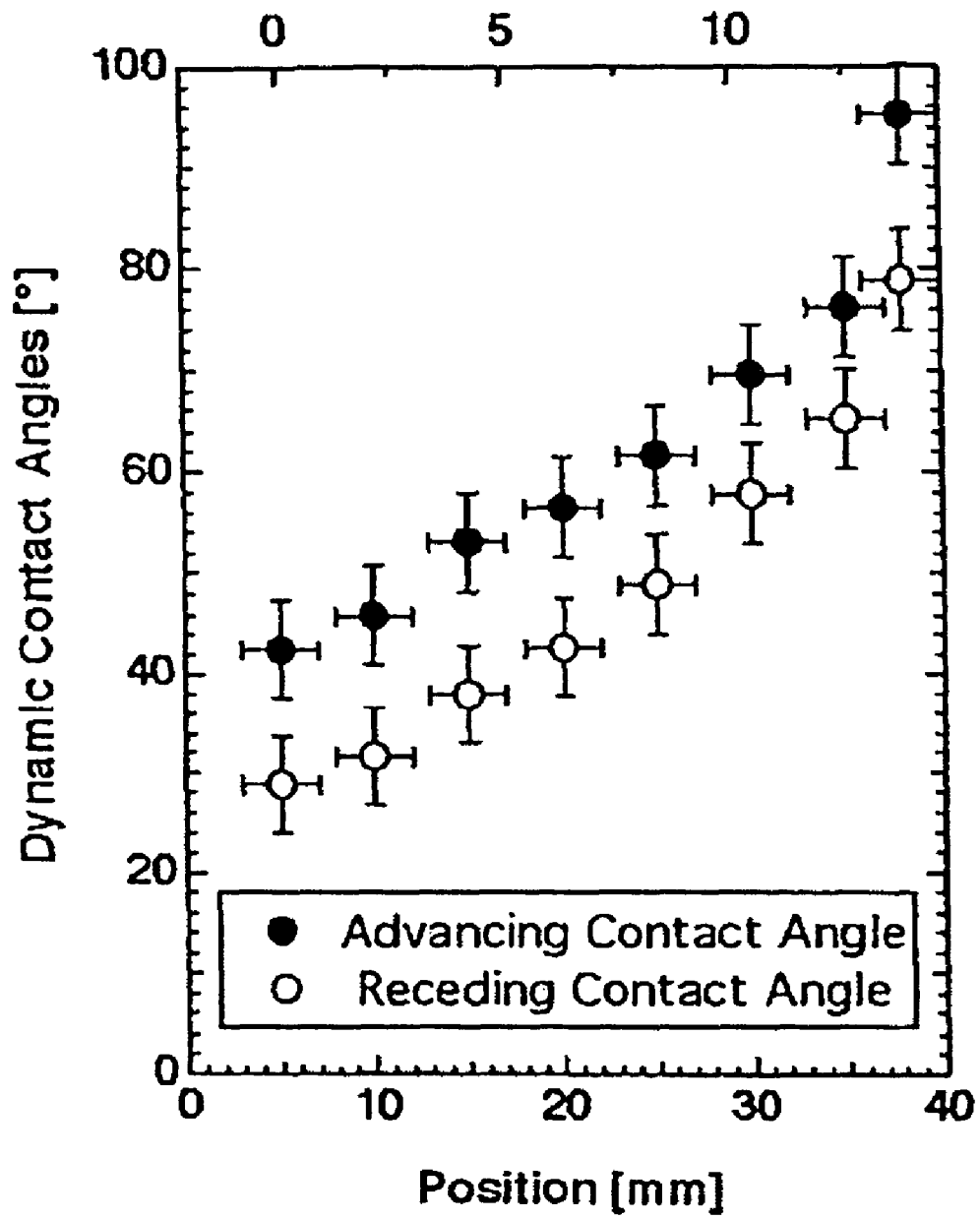

length = 40 mm

CONTROLLED SURFACE CHEMICAL GRADIENTS

CROSS-REFERENCE TO RELATED APPLICATIONS

This application claims benefit of U.S. Provisional Application No. 60/459,823, entitled "Controlled Hydrophobicity Gradients", to Nicholas D. Spencer et al., filed Mar. 31, 2003.

FIELD OF THE INVENTION

The present invention relates to surface-chemical gradients and processes for their production.

BACKGROUND OF THE INVENTION

The self-assembly of alkanethiols on gold is a well-known process that has been the subject of considerable research. (See e.g. Bain, C. D. et al., *J. Am. Chem. Soc.* 1989, 111, 321-335; Bain, C. D. and Whitesides, G. M. *J. Am. Chem. Soc.* 1988, 110. 6560-6561). The mechanisms leading to the formation of single-component and mixed self-assembled monolayers have been studied extensively. The mixed systems investigated have often consisted of methyl- and hydroxyl-terminated thiols since the results of adsorption can be readily monitored by water-contact-angle measurements. Such mixed monolayers were found to be stable and readily produced.

Chemical gradients are of great interest for numerous practical applications, such as investigating biomolecular interactions, cell-motility studies, diagnostics, nanotribology, or microfluidics, and naturally lend themselves to combinatorial studies, since an entire spectrum of chemical properties can be covered in a single experiment. A number of gradient preparation techniques for various substrates have been described (see e.g. Ruardy, T. G., et al., *Surf. Sci. Rep.* 1997, 29, 1-30; Liedberg, B. and Tengvall, P. *Langmuir,* 1995, 11, 3821-3827; Efimenko K., et al., *Macromolecules* 2003, 36, 2448-2453) and such gradients have been used for further experiments and applications (Herbert C. B., at al., *Chem. Biol.* 1997, 4, 731-737; Sehayek T., Vaskevich A. and Rubinstein I. *J. Am. Chem. Soc.* 2003, 125, 4718-4719). Several methods have been reported for the generation of thiol-based chemical gradients, including (1) the cross-diffusion of two thiol solutions through a polysaccharide matrix (Liedberg, B. and Tengvall, P. *Langmuir,* 1995, 11, 3821-3827), (2) applying an electrochemical potential to a substrate during adsorption (Terrill R. H., et al., *J. Am. Chem. Soc* 2000, 122, 988-989), (3) the use of microfluidic devices (Jeon N. L., et al., *Langmuir* 2000, 16, 8311-8316; Dertinger S. K. W., et al., *Anal. Chem.* 2001, 73, 1240-1246), and (4) scanning-tunneling-microscopy-based replacement lithography (Fuierer R. R., et al., *Adv. Mater.* 2002, 14, 154-157). With the exception of the electrochemical potential approach, the gradients formed have been limited in physical size. The electrochemical approach is a complicated process that is limited to forming gradients on conducting substrates.

Therefore it is an object of the invention to find a simpler method for fabricating chemical gradients of adsorbate monolayers on a variety of substrates.

It is also an object of the invention to provide a method for fabricating chemical gradients of adsorbate monolayers that are of the order of one cm or longer.

BRIEF SUMMARY OF THE INVENTION

A simple and reproducible preparative method for the fabrication of surface-chemical gradients is described herein. Surface-chemical gradient films are prepared from a dilute solution of one adsorbate by moving a liquid boundary in relative motion to the substrate surface. In one embodiment, this is accomplished by using a linear-motion drive to gradually immerse samples into the solution. The surface is subsequently saturated by means of immersion into a dilute solution of another adsorbate. As demonstrated by X-ray photoelectron spectroscopy (XPS), the self-assembled monolayer gradient produced in this way displays a high packing density. This method can be used in the preparation of gradients of various chemical or biochemical functionalities in one or two dimensions. Such gradients can be used in a wide variety of applications in such diverse areas as cell-motility studies, nanotribology research, and high-throughput screening.

BRIEF DESCRIPTION OF THE DRAWINGS

FIG. 1a is a graph of dynamic contact angles (°) along a gradient involving two adsorbates, one of which has a hydrophilic endgroup (—OH) and the other a hydrophobic endgroup (—$CH_3$). Advancing (●) and receding (○) contact angles are represented on the graph.

DETAILED DESCRIPTION OF THE INVENTION

I. Methods for Making Chemical Gradients

Figure 1B:
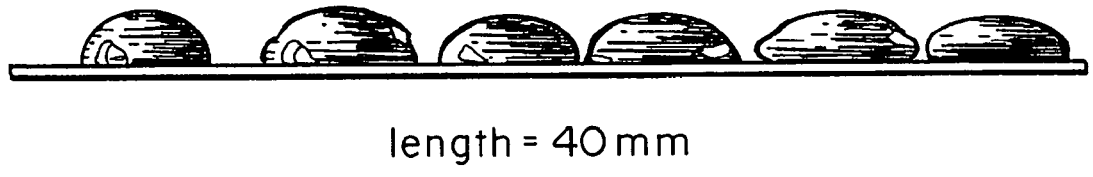
FIG. 1b is a drawing of water droplets along a wettability gradient.

Surface-chemical gradient films are prepared by using an adsorbate-containing liquid boundary that is in relative motion to the substrate. Different surface-chemical concentrations of separate samples (e.g. hydrophobicity values) can be produced on a single substrate if the immersion time is translated into a spatial distribution, which thereby generates a gradient. In one embodiment, this is accomplished through a controlled immersion of a substrate into a solution of adsorbate by means of a linear-motion drive. In a second embodiment, the moving liquid front is accomplished by means of a syringe and a syringe pump.

Optionally, the process involves a second step in which the surface is immersed in a second adsorbate solution that is different from the first solution. The second step is particularly useful for forming complete monolayers that incorporate a gradient.

A surface-chemical gradient film composed of a single component is a result of the varied coverage and packing of the adsorbate along the immersion axis of the substrate. Since partial monolayers are generally less ordered than full monolayers, this initial surface also displays a gradient in order. To remove this inhomogeneity to promote the formation of a complete monolayer while maintaining the surface-chemical gradient, the substrate is immersed in a second adsorbate solution in a second step. Generally, in the second step, a more concentrated adsorbate solution is used.

Optionally, the gradient may be formed using two perpendicular immersions into two separate adsorbates. This process forms a 2-dimensional chemical gradient.

A. Formation of Gradient Using a Linear-Motion Drive

In one embodiment, a surface concentration gradient of one type of adsorbate is achieved upon gradually immersing a substrate into very dilute adsorbate solution using a linear-motion drive. The position along the sample corresponds directly to a particular immersion time. Thus, the linear motion speed is carefully selected according to the adsorption kinetics.

The linear motion speed generally ranges from 0.1 µm/second to 10 cm/second, and is preferably 10-100 µm/second. These speeds allow for a controllable linear motion drive.

Typical speed ranges are from 1 µm/sec to 2.5 mm/sec. The speeds used to form the gradients described in the examples are as follows. For the $OH$—/$CH_3$-gradient (5 µM 1-mercapto-11-undecanol ($HO(CH_2)_{11}SH$) and 10 µM dodecanethiol ($CH_3(CH_2)_{11}SH$)) the speed was 50 µm/sec for OH-terminated thiol solution, followed by overnight immersion in the $CH_3$-terminated thiol solution. The speed for the $COOH$—/$CH_3$-gradient (10 µM (1-mercapto-11-undecanol ($COOH(CH_2)_{11}SH$) and 5 µM dodecanethiol ($CH_3(CH_2)_{11}SH$)) was 75 µm/sec for $CH_3$-terminated thiol solution, followed by overnight immersion in the COOH-terminated thiol solution. The speed for the $CF_3$—/$CH_3$-gradient (5 µM 1H,1H,2H,2H,-perfluorodecane-1-thiol ($CF_3(CF_2)_7(CH_2)_2SH$) and 10 µM dodecanethiol ($CH_3(CH_2)_{11}SH$)) was 200 µm/sec for $CF_3$-terminated thiol solution, followed by overnight immersion in the $CH_3$-terminated thiol solution.

B. Formation of a Gradient Using a Syringe Pump

In a second embodiment, the needle of a syringe pump is placed in close proximity to the substrate surface, such that upon operating the syringe (by means of a syringe pump) a spreading growing droplet of the first dilute adsorbate solution is produced on the surface. This creates a local, radially symmetrical gradient on the surface with similar compositional ranges to those obtained using a linear motion gradient. The second immersion step involves immersion of the sample into a second adsorbate solution.

C. Second Immersion Step

Following the first adsorption sep, the substrate may be immersed in a complementary adsorbate solution, providing a surface-chemical gradient within a monolayer over a significant distance. Complementary pairs of adsorbates (i.e. the first and second solutions) include long-chain ($C_{12}$-$C_{20}$) thiols, terminated with different end groups, such that one end group is bioactive, or hydrophilic and the other end group is inert or hydrophobic. Virtually any combination of end groups could be used. The combination of end groups is selected based on the specific surface-chemical purpose. Suitable end group pairs include: —$CH_3$/—$OH$, —$CH_3$/—$COOH$, —$CH_3$/—$CF_3$, and —$OCH_3$/biotin.

D. Surfaces

The substrate may be formed of a wide range of materials. Suitable materials include glass, metals, oxides, and synthetic polymeric surfaces. The surface may be a glass or silicon surface that has be treated to contain a gold layer on the top. The surface may be the surface of a silicon wafer or other semiconductor. The choice of surface is determined by the adsorbate-substrate interaction.

The surface can be long or short. Suitable lengths range from 1 mm to 1 centimeter, or longer. In the preferred embodiment, the length of the surface is 1 cm or longer, and typically ranges from 1 cm to 5 cm. The length of the substrate may be 10 cm or greater.

E. Adsorbate Solutions Used to Form Gradients

Any solution containing a compound that adsorbs onto the surface of the substrate can be used. In a preferred embodiment, the surface is a gold surface and the adsorbate solution contains a thiol. Suitable thiols include alkane thiols, such as methyl-terminated thiols with varying hydrocarbon chain length, $CH_3(CH_2)_nSH$, where n=4–18; hydroxyl-terminated thiols with varying hydrocarbon length, $OH(CH_2)_nSH$, where n=8-18, carboxylic-terminated thiols with varying hydrocarbon chain length, $HOOC(CH_2)_nSH$, where n=8–18; and 1H,2H,2H,2H-perfluordecane-1-thiol (($CF_3(CF_2)_7(CH_2)_2SH$). Optionally, the alkanes are end-functionalized with reactive groups. Such reactive groups include biotin, vinylsulfone, maleimide, or N-hydroxy succinimide. These reactive groups may be coupled to biomolecules to prepare a biochemical gradient. The biomolecules may be any bioactive molecule, including for example peptides, proteins, oligosaccharides, polysaccharides, DNA, RNA, or lipids.

Additionally, linear and radial gradients may be produced on, for example, oxidized silicon wafers, by means of two different adsorbing polyelectrolytes, such as poly (L-lysine)-g-poly(ethylene glycol), with or without end functionalization. The end-functionalized molecules may be coupled to biomolecules to form a biochemical gradient.

The concentration of the adsorbing solution typically ranges from 0.1 µM to 0.1 M. Preferably the concentration ranges from 1 µM to 1 mM. The concentration is selected, along with the speed, to produce a surface where the concentration of the adsorbate increases from one end to the opposite end. Thus one end contains little or none of the first adsorbate, while the other end is fully saturated, or nearly saturated with the first adsorbate. If a second adsorbate is added, it has an opposite concentration gradient to the concentration gradient of the first adsorbate.

II. Chemical Gradients

The surface-chemical gradients may form hydrophobicity gradients, where the hydrophobicity/hydrophilicity of the surface increases or decreases along the length (or radius) of the substrate surface, or gradients that contain bioactive molecules, where the concentration of bioactive molecule increases or decreases along the length (or radius) of the substrate surface. The gradients are typically self-assembled monolayers (SAM).

Figure 2:
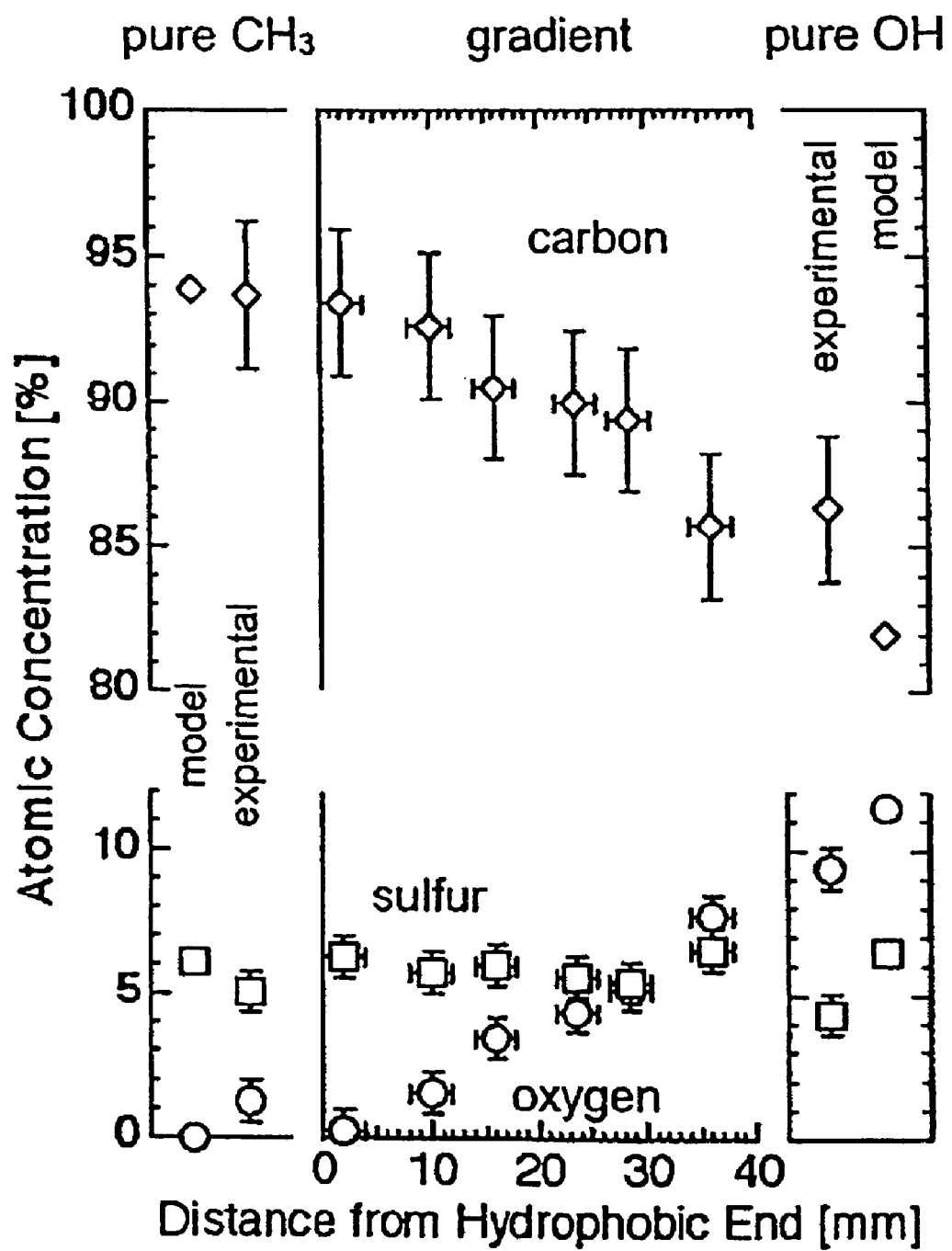
FIG. 2 is a graph of atomic concentrations (%) along a wettability (—$CH_3$/—OH) gradient (distance (mm) from hydrophobic end) as measured by XPS.

The surface-chemical gradients produced using the processes described herein display a high packing density, as demonstrated by the low hysteresis in dynamic contact angle (FIG. 1a) and x-ray photoelectron spectroscopy (XPS) measurements (FIG. 2).

For a full monolayer on gold formed using alkanethiols, a constant sulfur concentration (about 6 atomic %) is expected across the whole gradient. At the same time, the normalized atomic concentration of oxygen increases from the hydrophobic to the hydrophilic side, while the amount of carbon decreases since the end methyl groups are increasingly replaced by hydroxyl groups.

The gradients may be one-dimensional or two-dimensional gradients.

III. Applications for Gradients

This method can be used in the preparation of gradients of various chemical or biochemical functionalities in one or two dimensions. Such gradients can be used in a wide variety of applications including cell-motility studies and other biological investigations, diagnostics, microfluidics, nanotribology research, and high-throughput screening. Gradients may be used, for example, to determine the sensitivity of cells to specific surface species, to sort cells, identify microorganisms, and test surface-bound pharmaceuticals' influence on cells. Gradients can also be used to investigate any physical property that might depend on the surface concentration of a particular species, including friction, lubrication, wear, or adhesion.

The methods and compositions described herein will be further understood by reference to the following non-limiting examples.

EXAMPLES

Example 1

Preparation of Gradient SAM Films

The two alkanethiols employed were dodecanethiol ($CH_3(CH_2)_{11}SH$) and 11-mercapto-1-undecanol ($HO(CH_2)_{11}SH$), both from Aldrich Chemicals (Milwaukee, Wis., USA). Ethanol (purity >99.8%, Merck, Darmstadt, Germany) was used as a solvent. The substrates for SAM films were prepared by evaporating gold (purity >99.99%, Unaxis, Balzers, Liechtenstein) onto silicon wafers (POWATEC, Cham, Switzerland), according to a standard method. (Bain, C. D., et al., *J. Am. Chem. Soc.* 1989, 111, 321-335) The silicon wafers were coated with a 6 nm-thick chromium adhesion layer, followed by an 80 nm gold film in an evaporation chamber (MED 020 coating system, BALTEC, Balzers, Liechtenstein) at a pressure of ca. $2 \cdot 10^{-5}$ mbar. All glassware was cleaned with piranha solution (7:3 concentrated $H_2SO_4$/30% $H_2O_2$) for 20 minutes and rinsed copiously with deionized water and ethanol. The stock solutions were prepared by dissolving $CH_3(CH_2)_{11}SH$ or $HO(CH_2)_{11}SH$ in ethanol at a concentration of 1 mM. All other solutions were prepared by further dilution of the corresponding stock solution.

The gradient SAM films were generated by varying the immersion time in alkanethiol-containing solutions along the longitudinal axis of the gold-coated silicon substrate (length 4 cm, width 1 cm). The immersion speed was 50 μm/sec. Thus, one end of 4 cm-long substrate was immersed for 800 sec (13 min and 20 sec) and the other end was immersed for less than a second. The variation of immersed time along the substrate was linear. The immersion of the substrates was controlled by a computer-driven linear-motion drive (OWIS, Staufen, Germany). All substrates were rinsed with ethanol, dried with nitrogen and plasma cleaned (30s $N_2$, high power, Harrick Plasma Cleaner/Sterilizer PDC-32G instrument, Ossining, N.Y., USA) before immersion. Before characterization, the substrates were again rinsed with ethanol and dried with nitrogen.

Characterization of Gradient SAM Films

The hydrophobicity variation of the gradient SAM films was characterized by water-contact-angle measurements as a function of position along the longitudinal axis of the sample. Both static and dynamic contact angles were measured employing a contact-angle goniometer (Ramé Hart model 100, Ramé Hart Inc., Mountain Lakes, N.J., USA and G2/G40 2.05-D, Krüss GmBH, Hamburg, Germany, respectively). The results of dynamic contact-angle measurements were evaluated using digital image analysis. X-ray photoelectron spectra were obtained using a PHJ 5700 spectrometer with an Al Kα source (350 W, 15 kV) at a take-off angle of 45°. A pass energy of 46.95 eV and 0.1 eV per step was used to keep the exposure time and, therefore, X-ray damage to a minimum while having reasonable signal-to-noise ratios. The exposure time for each measurement of the four regions (C1s, O1s, S2p and Au4f) was 700 s.

Results and Discussion

In previous studies, the kinetics of alkanethiol adsorption on gold substrates have been investigated by varying the exposure time of a series of samples in solutions containing alkanethiol moieties. (See e.g. Bain, C. D. et al., *J. Am. Chem. Soc.* 1989, 111, 321-335; Bain, C. D. and Whitesides, G. M. *J. Am. Chem. Soc.* 1988, 110. 6560-6561). This approach was reproduced for both $CH_3(CH_2)_{11}SH$ and $HO(CH_2)_{11}SH$ at different concentrations. In all cases, water-contact angles (static) after 24 hours of immersion reached saturated values. The adsorption behavior in the initial stages (<30 min) shows a strong dependence on the solution concentration and the type of alkanethiol. For the highly concentrated solution (1 mM), both thiols ($CH_3(CH_2)_{11}SH$ and $HO(CH_2)_{11}SH$) reached water-contact angles with less than 5% deviation from the saturated monolayer values immediately after immersion (<1 min), while systematically longer times were needed to reach these values for more dilute solutions (0.01 mM and 0.0033 mM). Further, $HO(CH_2)_{11}SH$ displayed a slower adsorption behavior than $CH_3(CH_2)_{11}SH$, presumably due to its greater affinity for ethanol.

In this example, a concentration of 3.3 μM and a linear motion speed of 40 μm/sec were used in the first step. Then, the sample was immersed in the complementary thiol solution in a second step.

Two approaches have been employed for the second immersion step: (a) the sample was immersed in the same way as in the first step, allowing the end that was least exposed to the first component to be initially immersed in the complementary solution ("head-to-tail method"); or (b) following the initial step, the sample was fully immersed in the complementary solution for a given time ("full-immersion method"). To facilitate the filling of vacant binding sites, a higher concentration (0.01 mM) was selected for the second solution. The samples were rinsed with ethanol and blown dry with a stream of nitrogen prior to their immersion into the second solution.

Both alternatives showed that the hydrophobicity gradient range is extended after immersion into the second solution. However, in terms of monolayer completion and reproducibility/stability, the full-immersion step provided the best results.

The advancing and receding contact-angle measurements obtained from overnight full immersion are shown in FIG. 1(*a*). In this plot, the results obtained from five different gradient films are plotted to show their reproducibility (±5°). A fairly linear hydrophobicity gradient with an average water-contact-angle slope of 1.5°/mm over 35 mm is obtained. The average water contact angle hysteresis of 14° between advancing and receding contact angles indicates that the monolayer formation is nearly complete along the gradient. (Bain, C. D et al., *J. Am. Chem. Soc.* 1989, 111, 321-335)

The drawing in FIG. 1(*b*) provides a two dimensional image of the water droplets along a hydrophobicity gradient generated by the full-immersion method on a surface with a length of 40 mm.

The chemical composition of such a gradient was also characterized by XPS immediately after preparation. An almost linear increase for the oxygen 1 s, with a concomitant decrease in the carbon Is signals, was found in the experiment, in agreement with the contact-angle results (see FIG. 2). The comparison of the two extreme ends of the gradient with two control samples immersed for 24 hours in either 0.003 mM $HO(CH_2)_{11}SH$ or 0.003 mM $CH_3(CH_2)_{11}SH$ demonstrates that the chemical composition is changing from an almost complete monolayer of $CH_3(CH_2)_{11}SH$ to an almost complete monolayer of $HO(CH_2)_{11}SH$ in a very smooth and nearly linear manner. The composition of the pure monolayers was compared with a theoretical model, where the attenuation effects of the monolayer and take-off angle of 45° were corrected for. (Laibinis, P. E., et al., *J. Phys. Chem.* 1991, 95, 7017-7021) In the case of the pure $CH_3(CH_2)_{11}SH$ sample, a perfect agreement was observed, whereas in the case of the pure $HO(CH_2)_{11}SH$ sample, an excess of carbon was found. This can be explained by a higher affinity to carbon contamination by the higher-surface-energy samples, compared to the low-surface-energy, hydrophobic methyl-terminated surfaces. This explanation is in good agreement with results from ellipsometry, where films fabricated from $HO(CH_2)_{11}SH$ are always found to be a few Angstroms (Å) thicker than $CH_3(CH_2)_{11}SH$ films. (Liedberg, B. and Tengvall, P. *Langmuir,* 1995, 11, 3821-3827; Liedberg, B., et al., U. *Langmuir* 1997, 13, 5329-5334). If a monolayer of carbonaceous contamination is assumed to be present on the OH-terminated surface, the calculated normalized atomic concentrations match experimental values within the error bars.

Both ends are in good agreement with samples immersed in either single component: $CH_3(CH_2)_{11}SH$ or $HO(CH_2)_{11}SH$. Theoretical values for a full $CH_3$ terminated thiol film or for a full OH terminated thiol film were calculated using a 15 Å thick model (value from ellipsometry and modeling; electron take off angles of 45°: attenuation length of 0.085*(kinetic energy)$^{0.5}$). The discrepancy between the calculated and experimental values in the case of the OH terminated film can be explained with additional carbon contamination of the hydrophilic sample.

Example 2

Preparation of a Wettability Gradient (50° to 105° in Water-Contact Angle)

A hydrophobicity gradient that covers a higher range of water-contact angle can be generated by gradually immersing a cleaned gold-coated silicon wafer of 4 cm×1 cm size into 5 µM 1-mercapto-11-undecanol ($HO(CH_2)_{11}SH$) solution at a speed of 50 µm/s. Once the sample is completely immersed, it is pulled out at a speed of 2.5 mm/s, rinsed with ethanol and dried with nitrogen. After an overnight immersion into 10 µM dodecanethiol ($CH_3(CH_2)_{11}SH$), a gradient of 50° to 105° in water-contact-angle is generated.

Example 3

Preparation of a Wettability/Charge Gradient (15° to 75° in Water-Contact Angle)

Hydrophobicity gradients can also be prepared by combining methyl-terminated thiols ($CH_3(CH_2)_{11}SH$) with carboxyl-terminated thiols ($HOOC(CH_2)_{10}SH$). A cleaned gold-coated silicon wafer of 4 cm×1 cm size is was immersed into 5 µM dodecanethiol ($CH_3(CH_2)_{11}SH$) solution at a speed of 75 µm/s until the whole sample is was immersed. Then it was retracted at a speed of 2.5 mm/s, rinsed with ethanol and dried with nitrogen. After an overnight immersion into 10 µM 11-Mercaptoundecanoic acid ($HOOC(CH_2)_{10}SH$) solution, a gradient of 15° to 75° in water-contact-angle was generated.

Example 4

Preparation of a Fluorine-Concentration Gradient

Fluorine-concentration gradients can be prepared by a similar method described above. A cleaned gold-coated silicon wafer of 4 cm×1 cm was immersed into 5 µM ethanolic 1H,1H,2H,2H,-perfluorodecane-1-thiol ($CF_3(CF_2)_7(CH_2)_2SH$) solution at a speed of 200 µm/s until the whole sample was immersed. After the sample was rinsed with ethanol and dried with nitrogen, it was immersed into 10 µM ethanolic solution of 1-dodecanethiol ($CH_3(CH_2)_{11}SH$) overnight. The chemical analysis of the sample by X-ray photoelectron spectroscopy (XPS) shows that fluorine concentration linearly extends from 0 atomic % (methyl-rich side of the gradient) to 20 atomic % (fluorine-rich side of the gradient), whereas the carbon concentration decreased from 95 atomic % to 75 atomic %. The wettability of fluorine-rich and methyl-rich part of the gradient is not distinguishable by water. Thus, fluorine-concentration gradients can offer, for instance, friction force gradients in the absence of the variation in capillary forces.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for preparing a surface-chemical gradient on a substrate comprising selecting a speed at which the substrate will be exposed to an advancing front of a first solution comprising a first adsorbate, wherein the speed is selected based on the adsorption kinetics of the first adsorbate onto the surface of the substrate, exposing the substrate to the advancing front of the first solution, wherein the substrate is exposed to the advancing front of the first solution for a time period sufficient to adsorb the first adsorbate onto the surface of the substrate in an amount decreasing in concentration from a first area on the substrate to a second area on the substrate.

2. The method of claim 1, further comprising exposing the surface of the substrate to a second solution comprising a second adsorbate.

3. The method of claim 1, wherein the surface-chemical gradient is a hydrophobicity gradient that changes the amount of water attracted to the surface of the substrate over the length of the surface of the substrate.

4. The method of claim 1, wherein the surface of the substrate is formed of a material selected from the group consisting of glass, metals, oxides, and synthetic polymers.

5. The method of claim 2, wherein the surface of the substrate is gold and the first and second solutions comprise alkanethiols.

6. The method of claim 2, wherein the surface of the substrate is an oxide and the first and second solutions comprise organic phosphates.

7. The method of claim 2, wherein the surface of the substrate is an oxide and the first and second solutions comprise polyelectrolytes.

8. The method of claim 2, wherein the surface of the substrate is a hydrophobic polymer and the first and second solutions comprise polyelectrolytes.

9. The method of claim 2, wherein the first or second adsorbate comprises a biomolecule.

10. The method of claim 1, wherein the surface of the substrate is exposed to the first solution using a linear-motion drive.

11. The method of claim 1, wherein the surface of the substrate is exposed to the first solution using a syringe pump.

12. The method of claim 2, wherein the surface of the substrate is exposed to the second solution by full immersion.

13. A method of using a surface-chemical gradient for biological analysis comprising exposing the surface-chemical gradient to cells, wherein the surface-chemical gradient comprises a first adsorbate in an amount decreasing in concentration from a first area on the substrate to a second area on the substrate and a second adsorbate in an amount increasing in concentration from the first area on the substrate to the second area on the substrate, wherein the surface gradient is radially symmetrical.

14. The method of claim 13, wherein the first or second adsorbate comprises a biomolecule.

15. A method of using a surface-chemical gradient for analysis comprising exposing the surface-chemical gradient to a molecule, wherein the surface-chemical gradient comprises a first adsorbate in an amount decreasing in concentration from a first area on the substrate to a second area on the substrate and a second adsorbate in an amount increasing in concentration from the first area on the substrate to the second area on the substrate, wherein the surface gradient is radially symmetrical, and wherein the molecule preferentially binds with the first adsorbate.

16. A surface-chemical gradient on a surface of a substrate comprising a first adsorbate in an amount decreasing in concentration from a first area on the substrate to a second area on the substrate and a second adsorbate in an amount increasing in concentration from the first area on the substrate to the second area on the substrate, wherein the surface gradient is radially symmetrical.

17. The surface-chemical gradient of claim 16, wherein the gradient is formed by exposing the substrate to an advancing front of a first solution comprising a first adsorbate, wherein the substrate is exposed to the first solution for a time period sufficient to adsorb the first adsorbate onto the surface in an amount decreasing in concentration from a first area on the substrate to a second area on the substrate, and exposing the substrate to a second solution comprising a second adsorbate.

18. The method of claim 13, wherein the biological analysis is selected from the group consisting of cell-motility studies, diagnostics, microfluidics, nanotribology research, and high-throughput screening.

* * * * *